US00PP23899P2

(12) United States Plant Patent
Beekenkamp

(10) Patent No.: US PP23,899 P2
(45) Date of Patent: Sep. 10, 2013

(54) ***LAVANDULA* PLANT NAMED 'BKLVDVLB'**

(50) Latin Name: *Lavandula angustifolia*
Varietal Denomination: Bklvdvlb

(75) Inventor: Annie Cornelia Beekenkamp, Maasdijk (NL)

(73) Assignee: Beekenkamp Plants B.V., Maasdijk (NL)

( * ) Notice: Subject to any disclaimer, the term of this patent is extended or adjusted under 35 U.S.C. 154(b) by 107 days.

(21) Appl. No.: 13/317,164

(22) Filed: Oct. 11, 2011

(51) Int. Cl.
*A01H 5/00* (2006.01)

(52) U.S. Cl.
USPC ..... Plt./445

(58) Field of Classification Search
USPC ..... Plt./445, 226
See application file for complete search history.

*Primary Examiner* — June Hwu
(74) *Attorney, Agent, or Firm* — C. A. Whealy

(57) ABSTRACT

A new and distinct cultivar of *Lavandula* plant named 'Bklvdvlb', characterized by its compact, upright and somewhat outwardly spreading plant habit; freely branching growth habit; dense and bushy plant form; early and freely flowering habit; light violet-colored flowers arranged in compact verticillasters; and good garden performance.

2 Drawing Sheets

Botanical designation: *Lavandula angustifolia.*
Cultivar denomination: 'BKLVDVLB'.

BACKGROUND OF THE INVENTION

The present invention relates to a new and distinct cultivar of *Lavandula* plant, botanically known as *Lavandula angustifolia* and hereinafter referred to by the name 'Bklvdvlb'.

The new *Lavandula* plant is a product of a planned breeding program conducted by the Inventor in Maasdijk, The Netherlands. The objective of the breeding program was to develop new compact and early flowering *Lavandula* plants with uniform plant habit and attractive flower coloration.

The new *Lavandula* plant originated from an open-pollination in July, 2006 of *Lavandula angustifolia* 'Blue River', not patented, as the female, or seed, parent with an unknown selection of *Lavandula angustifolia*. The new *Lavandula* plant was discovered and selected by the Inventor in August, 2007 as a single flowering plant within the progeny of the stated open-pollination in a controlled outdoor nursery environment in Maasdijk, The Netherlands.

Asexual reproduction of the new *Lavandula* by terminal cuttings in a controlled greenhouse environment in Maasdijk, The Netherlands since September, 2007 has shown that the unique features of this new *Lavandula* plant are stable and reproduced true to type in successive generations.

SUMMARY OF THE INVENTION

Plants of the new *Lavandula* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Bklvdvlb'. These characteristics in combination distinguish 'Bklvdvlb' as a new and distinct *Lavandula* plant:

1. Compact, upright and somewhat outwardly spreading plant habit.

2. Freely branching growth habit; dense and bushy plant form.
3. Early and freely flowering habit.
4. Light violet-colored flowers arranged in compact verticillasters.
5. Good garden performance.

Plants of the new *Lavandula* differ from plants of the female parent, 'Blue River' primarily in the following characteristics:

1. Plants of the new *Lavandula* are more vigorous than plants of 'Blue River'.
2. Plants of the new *Lavandula* have larger flowers than plants of 'Blue River'.
3. Flowers of plants of the new *Lavandula* are lighter in color than flowers of plants of 'Blue River'.

Plants of the new *Lavandula* can be compared to plants of *Lavandula angustifolia* 'Thumbelina', not patented. Plants of the new *Lavandula* differ primarily from plants of 'Thumbelina' in the following characteristics:

1. Plants of the new *Lavandula* are more freely branching than plants of 'Thumbelina'.
2. Plants of the new *Lavandula* flower earlier than plants of 'Thumbelina'.
3. Plants of the new *Lavandula* have larger flowers than plants of 'Thumbelina'.
4. Flowers of plants of the new *Lavandula* are lighter in color than flowers of plants of 'Thumbelina'.

BRIEF DESCRIPTION OF THE PHOTOGRAPHS

The accompanying photographs illustrate the overall appearance of the new *Lavandula* plant showing the colors as true as it is reasonably possible to obtain in colored reproductions of this type. Colors in the photographs may differ slightly from the color values cited in the detailed botanical description which accurately describe the colors of the new *Lavandula* plant.

The photograph on the first sheet comprises a side perspective view of a typical flowering plant of 'Bklvdvlb' grown in a container.

The photograph on the second sheet is a close-up view of typical developing and fully developed flowering stems and upper and lower surfaces of leaves of 'Bklvdvlb'.

DETAILED BOTANICAL DESCRIPTION

The aforementioned photographs, following observations and measurements describe plants grown during the spring and summer in 12-cm containers in a glass-covered greenhouse in Maasdijk, The Netherlands and under cultural practices which approximate those generally used in commercial *Lavandula* production. Plants were 23 weeks old when the photographs and description were taken. Plants were pinched one time. During the production of the plants, day temperatures ranged from 15° C. to 22° C. and night temperatures ranged from 12° C. to 16° C. In the following description, color references are made to The Royal Horticultural Society Colour Chart, 2007 Edition, except where general terms of ordinary dictionary significance are used.

Botanical classification: *Lavandula angustifolia* 'Bklvdvlb'.

Parentage:

*Female, or seed, parent.*—*Lavandula angustifolia* 'Blue River', not patented.

*Male, or pollen, parent.*—Unknown selection of *Lavandula angustifolia*, not patented.

Propagation:

*Type.*—Terminal vegetative cuttings.

*Time to initiate roots, summer.*—About 28 days at 17° C. to 19° C.

*Time to initiate roots, winter.*—About 30 days at 18° C. to 19° C.

*Time to produce a rooted young plant, summer.*—About 45 to 48 days at 17° C. to 19° C.

*Time to produce a rooted young plant, winter.*—About 50 to 54 days at 17° C. to 19° C.

*Root description.*—Fine, fibrous; white in color.

*Rooting habit.*—Moderately freely branching; medium density.

Plant description:

*Form and growth habit.*—Herbaceous perennial; compact, upright and outwardly spreading plant habit; broad inverted triangle; moderately vigorous growth habit.

*Crop time.*—After rooting, about 23 weeks are required to produce finished flowering plants in 12-cm containers.

*Branching habit.*—Freely branching habit, dense and bushy plant form; about nine primary lateral branches per plant; pinching enhances lateral branch development.

*Plant height.*—About 27.1 cm.

*Plant width (spread).*—About 56.8 cm.

*Lateral branch description.*—Length: About 17.2 cm. Diameter: About 2 mm. Internode length: About 1 cm. Strength: Strong. Aspect: Upright to somewhat outwardly spreading. Texture: Tomentose. Color, immature: Close to 144A. Color, mature: Close to 165C and 199C.

*Foliage description.*—Arrangement: Opposite, simple; sessile. Length: About 5.5 cm. Width: About 6 mm. Shape: Lanceolate. Apex: Bluntly acute. Base: Cuneate. Margin: Entire. Texture, upper and lower surfaces: Tomentose. Fragrance: Aromatic, pungent. Venation pattern: Pinnate. Color: Developing leaves, upper and lower surfaces: Close to 191B. Fully expanded leaves, upper surface: Close to N137A; venation, close to N137A. Fully expanded leaves, lower surface: Close to 137B; venation, close to 137B and 143A.

Flower description:

*Flower arrangement and shape.*—Single flowers arranged in compact verticillasters; freely flowering habit, about 90 flowers per verticillaster; flowers salverform with a two-lobed upper lip and a three-lobed lower lip.

*Natural flowering season.*—Long flowering period; flowering continuous throughout the summer in The Netherlands; early flowering habit, plants begin flowering about 145 days after planting.

*Flower longevity on the plant.*—Flowers last about ten days on the plant; flowers not persistent.

*Fragrance.*—None detected.

*Flower buds.*—Length: About 6 mm. Diameter: About 2 mm. Shape: Oblong. Color: Close to 145A; towards the apex, close to 147C; pubescence, close to 83C and 157D.

*Inflorescence size.*—Height: About 8.3 cm. Diameter: About 2.3 cm.

*Flowers.*—Diameter: About 9 mm. Depth (height): About 1 cm.

*Petals.*—Lip length: About 1.1 cm. Lip width: Upper lip, about 6 mm; lower lip, about 9 mm. Lip shape: Roughly spatulate. Lip: Rounded. Lip margin: Entire. Lip texture, upper and lower surfaces: Smooth, glabrous. Color: When opening, upper and lower surfaces: Lip, close to N88D; tube, close to 92D. Fully opened, upper and lower surfaces: Lip, close to 85C; tube, close to 92D; color becoming closer to 94A to 94B with development.

*Flower bracts.*—Arrangement: Each whorl of flowers subtended by a dry flower bract. Length: About 3 mm. Width: About 3 mm. Shape: Broadly rhomboidal. Apex: Cuspidate. Base: Cuneate. Margin: Entire. Texture, upper and lower surfaces: Smooth, glabrous. Color, immature and mature, upper surface: Close to 164B.

*Sepals.*—Arrangement: Five sepals fused into a campanulate tube. Length: About 5 mm. Width: About 0.5 mm. Shape: Lanceolate. Apex: Broadly acute. Margin: Entire. Texture, upper surface: Smooth, glabrous. Texture, lower surface: Tomentose. Color, immature and mature, upper surface: Close to 145B. Color, immature and mature, lower surface: Close to 145A; towards the apex, close to 147C; pubescence, close to 83D and 157D.

*Peduncles.*—Length: About 25.5 cm. Diameter: About 2 mm. Strength: Strong. Aspect: Mostly upright. Texture: Tomentose. Color: Close to 144A; pubescence, close to 192D.

*Pedicels.*—Length: About 2 mm. Diameter: About 1 mm. Strength: Moderately strong. Aspect: About 50° from vertical. Texture: Tomentose. Color: Close to 145D.

*Reproductive organs.*—Stamens: Quantity per flower: Four. Filament length: About 1 mm. Anther shape: Reniform. Anther length: About 0.5 mm. Anther color: Close to 197B to 197D. Pollen amount: Moderate to abundant. Pollen color: Close to 24A. Pistils: Quantity per flower: One. Pistil length: About 5 mm. Stigma shape: Narrowly club-shaped. Stigma color:

Close to 156D. Style length: About 4 mm. Style color: Close to 156D. Ovary color: Close to 146B.

*Seeds and fruits*.—Seed and fruit development have not been observed on plants of the new *Lavandula*.

Disease/pest resistance: Plants of the new *Lavandula* have not been noted to be resistant to pathogens and pests common to *Lavandula*.

Garden performance: Plants of the new *Lavandula* have exhibited good tolerance to rain, wind and temperatures up to about 40° C. and are hardy to USDA Hardiness Zone 7.

It is claimed:

1. A new and distinct *Lavandula* plant named 'Bklvdvlb' as illustrated and described.

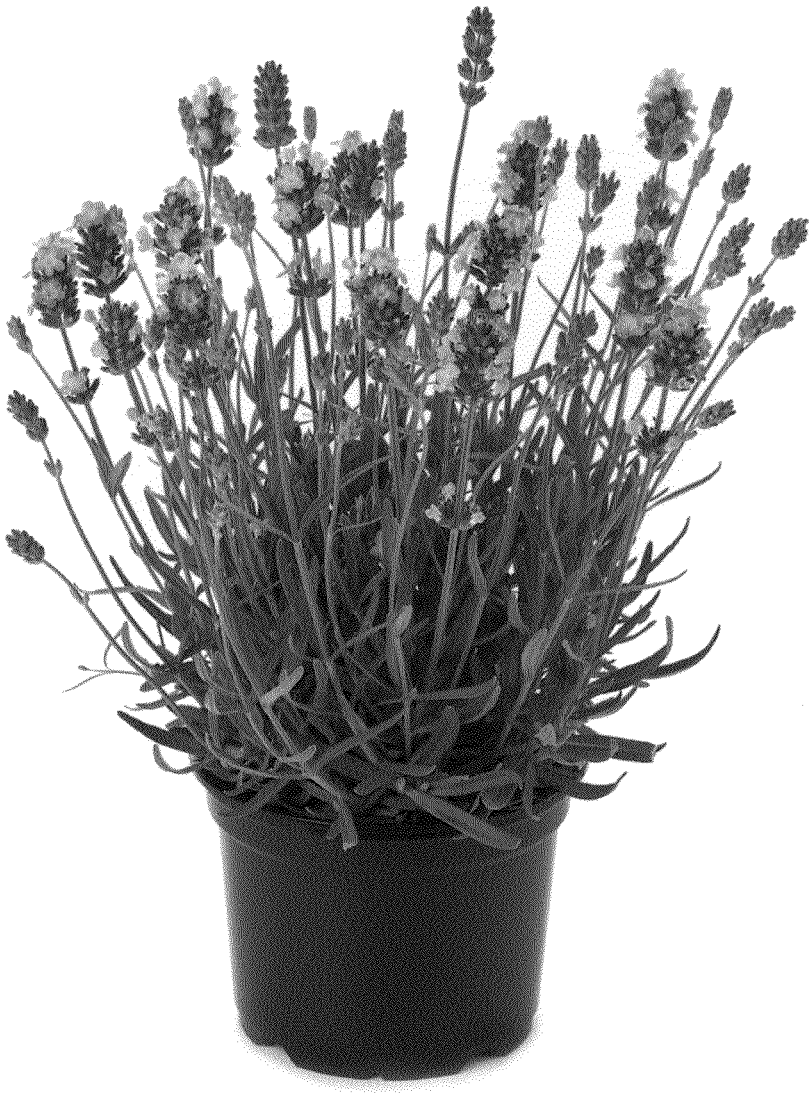

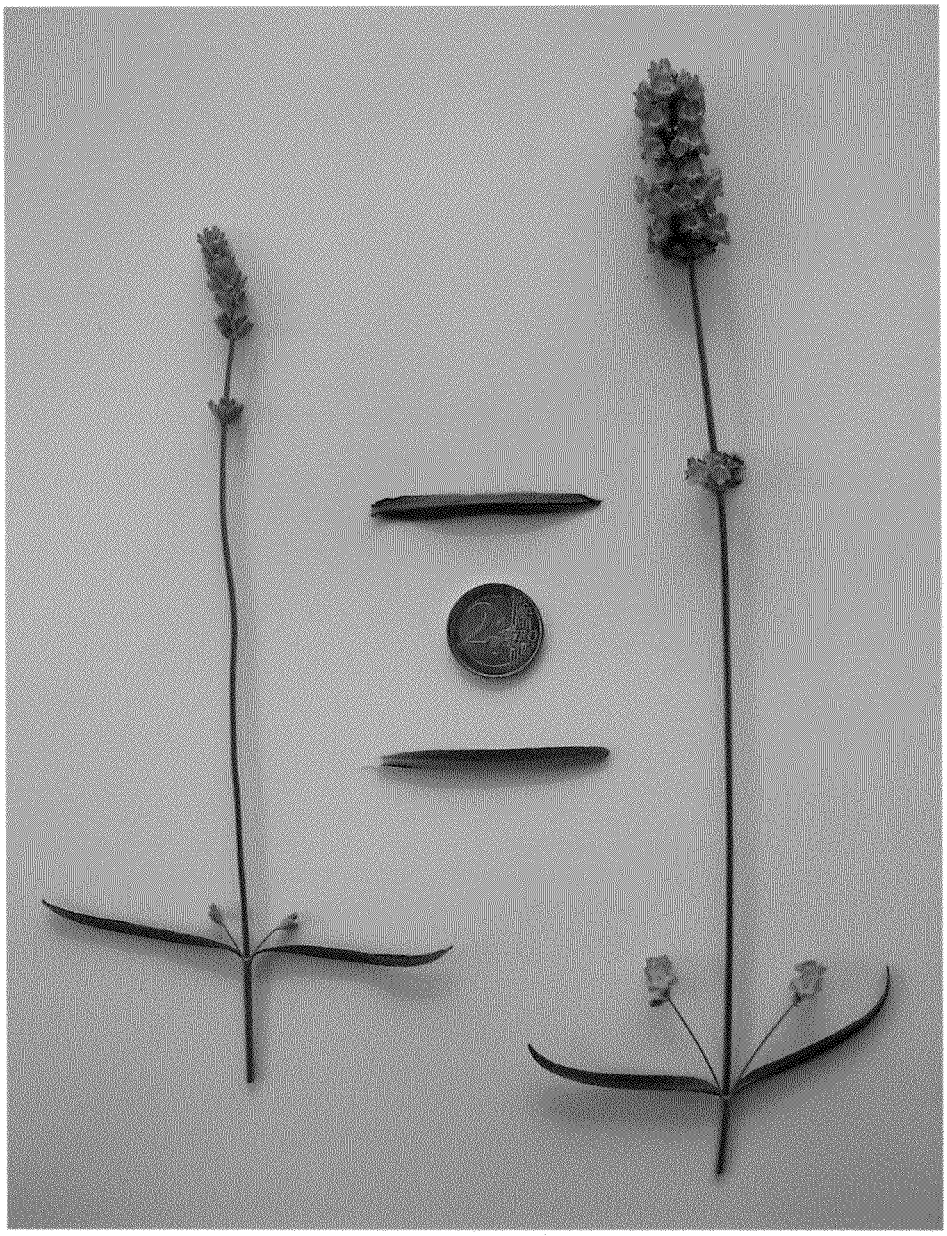

* * * * *